United States Patent [19]

Butler et al.

[11] 4,226,599
[45] Oct. 7, 1980

[54] REMOVAL OF HEPARIN FROM HEPARIN-CONTAINING BLOOD PLASMA SAMPLES USING A TRIETHYLAMINOETHYL CELLULOSE TABLET

[75] Inventors: James R. Butler, Morris Plains; James E. Turner; Frank W. Goodhart, both of Morristown, all of N.J.

[73] Assignee: Warner-Lambert Company, Morris Plains, N.J.

[21] Appl. No.: 50,355

[22] Filed: Jun. 20, 1979

Related U.S. Application Data

[62] Division of Ser. No. 931,032, Aug. 4, 1978.

[51] Int. Cl.³ ............................................ G01N 31/00
[52] U.S. Cl. ...................................... 23/230 B; 536/21
[58] Field of Search ......................... 23/230 B; 536/21

[56] References Cited

U.S. PATENT DOCUMENTS

| | | | |
|---|---|---|---|
| 2,128,432 | 8/1938 | Ramage | 252/427 X |
| 2,687,990 | 8/1954 | Weisz | 252/427 X |
| 3,099,600 | 7/1963 | Toccaceli | 536/21 |
| 4,055,510 | 10/1977 | Peska | 252/426 |
| 4,122,250 | 10/1978 | Schmer | 536/21 |

FOREIGN PATENT DOCUMENTS 1195010  6/1965  Fed. Rep. of Germany .............. 536/21

OTHER PUBLICATIONS

Chemical Abstracts, 78:112325b (1973).
Nealon et al., "An Extracorporeal Device to Treat Barbiturate Poisoning," JAMA, Jul. 1966, vol. 197, No. 2, 158–160.
Thompson et al., "Removal of Heparin and Protamine from Plasma," J. Lab. Clin. Med., 88, 922–929 (Dec. 1976).

Primary Examiner—Sidney Marantz
Attorney, Agent, or Firm—Walter Patton; Stephen Raines; Albert H. Graddis

[57] ABSTRACT

A tableted form of fibrous triethylaminoethyl cellulose suitable for the removal of heparin from heparin-containing blood plasma. The tablet is composed of granular microcrystalline cellulose and fibrous triethylaminoethyl cellulose in a ratio of from about 5.4:1 to about 10:1. The triethylaminoethyl cellulose tablet, which is formulated to provide from about 5 to about 26 mg. of triethylaminoethyl cellulose per milliliter of plasma sample, is added to a heparin-containing blood plasma sample, the sample is agitated or allowed to stand for a time sufficient to permit adsorption of substantially all heparin present. The sample is then centrifuged and the remaining heparin-free plasma can be subjected to coagulation testing in order to determine the true clotting time.

5 Claims, No Drawings

REMOVAL OF HEPARIN FROM HEPARIN-CONTAINING BLOOD PLASMA SAMPLES USING A TRIETHYLAMINOETHYL CELLULOSE TABLET

This is a division of application Ser. No. 931,032 filed Aug. 4, 1978.

BACKGROUND OF THE INVENTION

1. Field of the Invention

The present invention relates to the removal of heparin from blood plasma test samples.

2. Description of the Prior Art

Heparin is widely used as a parenteral anticoagulant for the treatment of thromboembolic patients, for the prophylactic treatment of high risk embolic patients and to reduce the incidence of deep-vein thrombosis after major surgery. Thromboembolic conditions are characteristic of disease states such as coronary thrombosis, venous thrombosis, pulmonary embolism and the like. During treatment, it is necessary to determine the patient's clotting time in the absence of heparin, i.e., the true blood plasma clotting time. Thus, it is necessary to neutralize or remove the heparin from the sample of the patient's blood plasma prior to coagulation testing.

Conventionally, heparin is neutralized by reaction with protamine, as described by Allen, J. G., et al., "A Protamine Titration as an Indication of a Clotting Defect in Certain Hemorrhagic States", in J. Lab Clin. Med. 34:473–476 (1949) and by Perkins, H. A., "Neutralization of Heparin In Vitro with Protamine; A Simple Method of Estimating the Required Dose", J. Lab. Clin. Med. 48:223–226 (August, 1956). Polybrene, a synthetic polymerized quaternary ammonium salt, has also been used to neutralize heparin (see Godal, H. C., "A Comparison of Two Heparin Neutralizing Agents: Protamine and Polybrene", Scandinav. J. Clin. & Lab. Invest. 12:466–457, (1960).

While the above-mentioned procedures have been used successfully, a tedious titration is required since protamine and polybrene are soluble in plasma. Any excess not combined with heparin will remain in the plasma, frequently undetected, and interfere with the coagulation test. Thus, the accuracy of the coagulation test results are questionable. The fact that the titration method for neutralization of heparin is of limited accuracy has been recognized in the literature: differences of as much as 5 to 10 mcg. of heparin per milliliter of blood have been reported by Wright, J. S., et al., "Heparin Levels During and After Hypothermic Perfusion", in J. Cardiovas. Surg. 5:244–250 (1964).

In order to overcome the above-mentioned deficiencies, Thompson, et al. (J. Lab. Clin. Med. 88:922–929, Dec., 1976) developed a chromatographic technique for removing heparin and protamine from plasma samples. Columns of ECTEOLA-cellulose (a moderately basic anion exchange resin) were used to adsorb up to 300 U. of heparin from 1 milliliter of plasma; and columns of carboxymethyl cellulose (a cation exchange resin) were used to adsorb protamine. However, the preparation and use of ion exchange columns prior to testing plasma for clotting time is time consuming, cumbersome and inconvenient. Additionally, at least a milliliter of plasma sample is taken up by the ion exchange columns and is unavailable for further testing. This is a serious disadvantage in pediatric cases where only small amounts of plasma sample can be obtained for testing.

In view of the deficiencies of the conventional art methods, there is a need for a simple, rapid procedure for removal of heparin from blood plasma samples without adversely affecting subsequent coagulation testing of the plasma sample.

Co-pending application Ser. No. 931,033, filed Aug. 4, 1978 by Arthur L. Babson and James E. Turner, entitled REMOVAL OF HEPARIN FROM BLOOD PLASMA SAMPLES USING AN INSOLUBLE PROTAMINE REACTION PRODUCT, describes a method for removing heparin using an insoluble protamine/glutaraldehyde reaction product; and co-pending application Ser. No. 931,031 filed Aug. 4, 1978 by James E. Turner, James R. Butler and Arthur L. Babson, entitled REMOVAL OF HEPARIN FROM BLOOD PLASMA SAMPLES USING TRIETHYLAMINOETHYL CELLULOSE describes a method for removing heparin using fibrous triethylaminoethyl cellulose.

SUMMARY OF THE INVENTION

A diagnostic tablet composition for removing substantially all heparin from heparin-containing blood plasma samples contains from about 5.4 to about 10 parts by weight of granular microcrystalline cellulose per part by weight of fibrous triethylaminoethyl cellulose. The diagnostic tablet is formulated to provide from about 5 to about 26 mg of triethylaminoethyl cellulose per milliliter of heparin-containing blood plasma test sample. In use, the tablet is added to one milliliter of heparin-containing plasma sample; the tablet hydrates and when agitated, becomes suspended throughout the plasma sample. The sample is allowed to stand or is subjected to further agitation for a time sufficient to permit adsorption of substantially all heparin and formation of an insoluble triethylaminoethyl cellulose/heparin complex. Centrifugation removes substantially all of the complex formed as well as any free, uncomplexed table ingredients. The remaining uncontaminated plasma may be subjected to coagulation testing to determine the true clotting time of the plasma sample.

DESCRIPTION OF THE PARTICULAR EMBODIMENTS it has now been found that a diagnostic tablet composition containing triethylaminoethyl cellulose and granular microcrystalline cellulose which is formulated to provide from about 5 to 26 mg. of triethylaminoethyl cellulose per milliliter of plasma sample is capable of removing substantially all heparin from the plasma sample without substantially affecting the true clotting time. The ratio of microcrystalline cellulose to triethylaminoethyl cellulose in the diagnostic tablet of this invention is from about 5.4:1 to about 10:1. Typically, a diagnostic tablet suitable for use with 1 milliliter of blood plasma sample is formulated to contain from about 5 to about 26 mg. of triethylaminoethyl cellulose and from about 54 to about 170 mg. of microcrystalline cellulose. The preferred diagnostic tablet of this invention which is suitable for use with 1 milliliter of blood plasma sample contains about 60 mg. of microcrystalline cellulose and about 10 mg. of triethylaminoethyl cellulose.

The triethylaminoethyl cellulose used in the diagnostic tablet of this invention is a fibrous anionic exchange material prepared from highly purified cotton and wood celluloses having an ion exchange capacity between 0.3 and 0.8, preferably 0.50 and 0.62 milliequivalents/gram. The thread-like fibers of the triethylaminoethyl cellulose have an average diameter of 18 microns and length therein from 20 to 300 microns. A particularly preferred triethylaminoethyl cellulose having a pk value of approximately 9.5 is marketed commercially under the trade name CELLEX T by Bio-Rad Laboratories, Richmond, California.

The granular microcrystalline cellulose suitable for use in the diagnostic tablet of this invention is an insoluble nonfibrous powder dispersible in water prepared as described in U.S. Pat. No. 2,978,446 and U.S. Pat. No. 3,141,875. A particularly preferred mirocrystalline cellulose is marketed under the trade name AVICEL by American Viscose Corporation, Marcus Hook, PA.

The diagnostic tablet of this invention is prepared by blending the microcrystalline cellulose with the fibrous triethylaminoethyl cellulose and compressing the mixture to form a shaped tablet. While the shape and size of the tablet are not critical, for practical reasons, a small tablet suitable for immersion in a one milliliter sample of blood plasma is preferred. Larger tablets of various shapes are within the scope of this invention but such tablets generally would require the use of more plasma sample and are therefore not preferred.

The diagnostic tablets of this invention are formulated to provide from about 5 to about 26 mg. of triethylaminoethyl cellulose per milliliter of blood plasma test sample and have been found capable of removing up to about 50 units of heparin per milliliter of plasma sample. It would, of course, be possible to formulate diagnostic tablets containing additional quantities of triethylaminoethyl cellulose but the administration of even relatively high therapeutic doses of heparin rarely brings about blood levels of more than two units of heparin. Therefore, by formulating the diagnostic tablets of this invention to provide from about 5 to about 26 mg. of triethylaminoethyl cellulose per milliliter of blood plasma test sample, removal of substantially all heparin in any clinical plasma sample is assured.

According to the process of this invention, the above described diagnostic tablet is added to 1 milliliter of heparin-containing blood plasma test sample, allowed to hydrate and disintegrate within the sample. Brief, vigorous agitation is typically used to disintegrate and suspend the tablet. For a tablet containing larger amounts of triethylaminoethyl cellulose and microcrystalline cellulose, no further agitation is necessary; the plasma sample is allowed to stand for a time sufficient to permit adsorption of substantially all heparin in the plasma sample, generally for from about 15 to about 20 minutes. For a tablet containing lesser amounts of triethylaminoethyl cellulose and microcrystalline cellulose, gentle agitation, either continuously or intermittently, is required; preferably, the sample is agitated continuously for 5 to 15 minutes preferably for about 10 minutes or the sample may be agitated for about 10 seconds every 3 minutes for about 15 to 20 minutes. Using any of the above techniques, suspension of the triethylaminoethyl cellulose uniformly throughout the plasma sample is achieved and heparin is adsorbed. An insoluble triethylaminoethyl cellulose/heparin complex is formed. Centrifugation removes substantially all of the complex formed as well as any free, uncoomplexed tablet ingredients. All of the procedures described above are performed at room temperature. The remaining plasma is uncontaminated with heparin and aliquots may be taken directly for coagulation testing to determine the true clotting time of the plasma sample.

During the course of treatment, hospitalized thromboembolic patients often receive increasingly lower doses of heparin intravenously, together with an oral anticoagulant such as Cuomadin in an effort to maintain the patient on the orally administered drug prior to discharge. In such situations, the heparin removal test procedure of this invention cannot be used due to the combined effects of the additional drug on subsequent evaluation of clotting using the Activated Partial Thromboplastin Time (APTT) Test.

The following examples are provided to further illustrate the method of this invention:

EXAMPLE 1

PREPARATION OF DIAGNOSTIC TABLET

Screen 10 gm of triethylaminoethyl cellulose through a no. 30 mesh screen. Added 60 gm. of granular microcrystalline cellulose NF, blend well and compress slugs on a ⅝ inch flat face beveled edge punch and die, set at 650 mg weight and about 12–15 kg hardness (Heberlein). Pass the slugs through a mill fitted with a no. 8 mesh screen and blend. Compress the milled powder on an 8/32 inch flat face beveled edge punch and die set at 70 mg weight and about 4–5 kg. hardness. One thousand tablets are obtained. Each tablet contains 10 mg. of triethylaminoethyl cellulose and 60 gm of microcrystalline cellulose.

EXAMPLE 2

REMOVAL OF HEPARIN FROM BLOOD PLASMA TEST SAMPLE

Add 1 ml of the patient's plasma to a 10×75 ml plastic test tube. Add a tablet prepared as described in Example 1 to the test tube and allow to swell for 5 minutes at room temperature. Vigorously agitate the tube with the index finger until the tablet is uniformly distributed throughout the plasma. Mix, using a rocking aliquot mixer (20 to 30 rpm) at room temperature for ten minutes. Centrifuge at 1200×g for 5 minutes to remove the heparin/triethylaminoethyl cellulose complex and the uncomplexed tablet ingredients. Remove appropriate aliquots of plasma for coagulation testing being careful to avoid dislodging the cellulose adhering to the wall.

EXAMPLE 3

PREPARATION OF DIAGNOSTIC TABLET

Blend 26 gm of triethylaminoethyl cellulose with 140 gm of granular microcrystalline cellulose NF, for 20 minutes and compress slugs using a ⅝ inch flat-faced beveled edge punch and die at 550 mg weight and about 12–14 kg hardness (Heberlein). Pass the slugs through a mill fitted with a no. 8 mesh screen and blend for 10 minutes. Compress the milled powder on a 7/32 inch by 17/32 inch capsule-shaped punch at 160 mg weight and about 5–8 kg. hardness. About one thousand tablets are obtained. Each tablet contains 26 mg. of triethylaminoethyl cellulose and 140 gm of microcrystalline cellulose.

EXAMPLE 4

REMOVAL OF HEPARIN FROM BLOOD PLASMA TEST SAMPLE

Add 1 ml of the patient's plasma to a 10×75 ml. plastic test tube. Add a tablet prepared as described in Example 3 to the test tube and allow to swell for 5 minutes at room temperature. Vigorously agitate the tube with the index finger until the tablet is uniformly distributed throughout the plasma. Allow to stand at room temperature for 15 minutes. Centrifuge at 1200×g. for 5 minutes to remove heparin/triethylaminoethyl cellulose complex and the uncomplexed tablet ingredients. Remove appropriate aliquots of plasma for coagulation testing, being careful to avoid dislodging cellulose adhering to the wall.

We claim:

1. A method for removing substantially all heparin from a heparin-containing blood plasma test sample which comprises:

A. adding to 1 milliliter of plasma sample a diagnostic tablet comprising from about 5.4 to about 10 parts by weight of granular microcrystalline cellulose per part by weight of fibrous triethylaminoethyl cellulose, said tablet being formulated to provide from about 5 to about 26 mg of triethylaminoethyl cellulose per milliliter of plasma sample;

B. agitating (A) for a time sufficient to disintegrate the tablet and distribute the fibrous triethylaminoethyl cellulose throughout the plasma sample and permit the adsorption of heparin;

C. centrifuging (B) to remove substantially all of the insoluble triethylaminoethyl cellulose heparin complex formed in the plasma sample, together with uncomplexed tablet ingredients;

thereby obtaining a substantially heparin-free blood plasma sample suitable for coagulation testing.

2. A method according to claim 1 wherein, in step (A), the triethylaminoethyl cellulose in the diagnostic tablet has an ion exchange capacity between about 0.3 and 0.8 milliequivalents/gram.

3. A method according to claim 1 wherein, in step (A), the triethylaminoethyl cellulose in the diagnostic tablet has an ion exchange capacity between about 0.5 and 0.62 milliequivalents/grams.

4. A method according to claim 1 wherein, in step (B), the sample is agitated vigorously to disintegrate the tablet and then agitated gently to maintain the fibrous triethylaminoethyl cellulose distributed throughout the plasma sample for a time sufficient to permit adsorption of heparin.

5. A method according to claim 1 wherein, in step (C), the sample is agitated vigorously to disintegrate the tablet and then allowed to stand for a time sufficient to permit adsorption of heparin.

* * * * *